United States Patent [19]

Noda et al.

[11] Patent Number: 4,462,996

[45] Date of Patent: Jul. 31, 1984

[54] AQUEOUS SUSPENSION OF OXENDOLONE

[75] Inventors: Etsunosuke Noda, Yao; Yoshiharu Matukura, Ikoma; Akihiro Nagai, Toyono, all of Japan

[73] Assignee: Takeda Chemical Industries, Ltd., Osaka, Japan

[21] Appl. No.: 406,460

[22] Filed: Aug. 9, 1982

[30] Foreign Application Priority Data

Aug. 18, 1981 [JP] Japan ............................ 56-129517

[51] Int. Cl.$^3$ ............................................. A61K 31/56
[52] U.S. Cl. .................................................. 424/243
[58] Field of Search ......................................... 424/243

[56] References Cited

U.S. PATENT DOCUMENTS 3,856,829 12/1974 Hiraga et al. ................. 260/397.4

OTHER PUBLICATIONS

Chemical Abstracts, vol. 79 (1973), Par. 27596s.
Chemical Abstracts, vol. 83 (1975), Par. 84928.
Chemical Abstracts, vol. 83 (1975), Par. 136944g.

Primary Examiner—Elbert L. Roberts
Attorney, Agent, or Firm—Wegner & Bretschneider

[57] ABSTRACT

The present invention relates to a stabilized aqueous suspension of oxendolone, which contains 0.05 to 1.0 w/v percent of a nonionic surfactant and 0.01 to 0.25 w/v percent of a p-hydroxybenzoic acid ester.

The suspension satisfy the requirements of a pharmaceutical preparation and shows a prolonged activities of oxendolone without accompanying pain when it is injected.

5 Claims, No Drawings

AQUEOUS SUSPENSION OF OXENDOLONE

This invention relates to a stabilized aqueous suspension of oxendolone.

Oxendolone is a generic name for 16β-ethyl-17β-hydroxy-4-estren-3-one, and it is known that the compound as well as various esters thereof have potent antiandrogenic activity (U.S. Pat. No. 3,856,829).

With a meager solubility of 0.001% or less in water (25° C.), oxendolone is so sparingly soluble and so hydrophobic that if dispersed in water, its particles remain afloat, failing to give a suspension meeting requirements of a pharmaceutical preparation. Incidentally, an aqueous suspension as a pharmaceutical product must satisfy various requirements such as a uniform dispersion of active component particles, a proper sedimentation rate on standing, a good redispersibility of particles and a satisfactory passage through the needle bore (for injecable preparations).

To impart such qualities to a pharmaceutical product, it is generally practiced to incorporate a thickening agent such as sodium carboxymethylcellulose, methylcellulose or the like, or, to increase the hydrophilicity of the product, a surfactant. Such procedures, if applied to emulsification of oxendolone, would not lead to satisfactory results.

Under these circumstances the present inventors conducted an intensive study and found unexpectedly that when a nonionic surfactant and a p-hydroxybenzoic acid ester are added in suitable amounts to oxendolone or an ester thereof, the suspension characteristics of the compound are remarkably improved. This invention has been conceived and developed on the basis of the above finding.

This invention relates, therefore, to a stabilized aqueous suspension of oxendolone or an ester thereof characterized by containing 0.05 to 1.0 w/v % of a nonionic surfactant and 0.01 to 0.25 w/v % of the a p-hydroxybenzoic acid ester.

Referring to oxendolone or said ester thereof which is employed in the aqueous suspension of this invention, the ester may, for example, be lower alkylcarboxylic acid esters such as acetate, propionate, valerate, caprylate, caproate, or the like. The number of carbon atoms in the ester is preferably smaller than 7.

The non-ionic surfactant mentioned above includes, for example, sorbitan fatty acid esters such as polyoxyethylene sorbitan monolaurate (Tween 20, Polysorbate 20), polyoxyethylene sorbitan monopalmitate (Tween 40, Polysorbate 40), polyoxyethylene sorbitan monostearate (Tween 60, Polysorbate 60), polyoxyethylene sorbitan monooleate (Tween 80, Polysorbate 80), etc., hydrogenated castor oil polyoxyethylene glycol esters such as hydrogenated castor oil polyoxyethylene 40 Mol (HCO-40), 50 Mol (HCO-50), 60 Mol (HCO-60) and 80 MOL (HCO-80), etc., polyoxyethylene polyoxypropylene ethers such as Pluronic F 68 and Pluronic L 64 (Wyandotte Co., U.S.A.), various other polyethylene glycol alkyl ethers, fatty acid monoglycerides, etc. Particularly preferred are Tween 20, Tween 80, HCO-50 and HCO-60. In terms of HLB number, it is generally desirable to use surfactants whose HLB numbers are within the range of from 8 to 18.

The p-hydroxybenzoic acid ester is exemplified by lower alkyl esters such as methyl, ethyl, propyl, butyl and other esters. These p-hydroxybenzoic acid esters may be used either alone or as a mixture of two or more species in combinations with said surfactant.

The proportion of said surfactant employed in the present invention generally falls within the ranges from 0.05 to 1.0 w/v % and preferably from 0.1 to 0.5 w/v %, though it may vary with the concentration of oxendolone and the amount of p-hydroxybenzoic acid ester. At concentrations below 0.05 w/v % no uniform dispersion can be accomplished. If the amount of the surfactant is larger than 1.0 w/v %, it tends to encourage free settling and cause caking and other difficulties.

The proportion of p-hydroxybenzoic acid ester may also vary with the concentration of oxendolone, the amount of said surfactant added and the solubility of the p-hydroxybenzoic acid ester, and it ranges generally from 0.01 to 0.25 w/v % and preferably from 0.1 to 0.2 w/v %. If its proportion is less than 0.01 w/v %, there occurs a free dispersion system giving rise to hard cakes.

Oxendolone or its ester is generally used in the concentration of 5 to 20 w/v % and preferably in the range of 8 to 13 w/v %.

According to this invention, the aqueous suspension can be prepared by blending oxendolone or its ester, a non-ionic surfactant and a p-hydroxybenzoic acid ester in an optional order in accordance with per se known process. A preferred production procedure is as follows.

PRODUCTION EXAMPLE

Ten (10) grams of microcrystalline particles of oxendolone are dispersed in 25 ml of a 0.8% solution of Tween 80.

Separately, an aqeuous solution is prepared which contains 0.28% of ethyl p-hydroxybenzoate, 0.028% of propyl p-hydroxybenzoate, 1% of sodium carboxymethyl-cellulose, 16% of D-sorbitol and 2% of benzyl alcohol. This solution (50 ml) is added to the above oxendolone-Tween 80 solution and the mixture is made up to 100 ml with water and stirred well.

In the aqueous suspension according to this invention, it is of course possible to incorporate those auxiliary agents and additives which are commonly used in aqueous suspensions, e.g. thickening agents such as sodium carboxymethylcellulose, methylcellulose, etc. and isotonicating agents such as glucose, xylitol, inositol, sorbitol, mannitol, etc. It is also possible to incorporate local anesthetics such as benzyl alcohol, mepivacaine hydrochloride, procaine hydrochloride, etc. and preservatives such as chlorobutanol, phenol, etc.

Thus prepared aqueous suspensions of this invention satisfy the requirements for pharmaceutical use and, moreover, show a prolonged activities of oxendolone without accompaniing pain when it is injected.

EXAMPLE 1

Oxendolone: 10 w/v %
Sodium carboxymethylcellulose: 0.5
D-sorbitol: 8
Benzyl alcohol: 1

An aqueous suspension containing the above components is labeled Composition A. To aliquots of Composition A are added various stabilizers as indicated in Table 1 to prepare a series of preparations. These preparations were examined immediately after preparation and after 2 years of storage at room temperature for dispersion uniformity, sedimentation volume, redispersibility and ease of passage through the injection needle bore. The results are set forth in Table 1. It is apparent that the addition of stabilizers according to this invention produces remarkable effects.

TABLE 1

| Formula | | | Immediately after preparation | | After 2 years of storage at room temperature | | |
|---|---|---|---|---|---|---|---|
| | | | Dispersion uniformity | Passage through needle bore | Sedimentation volume | Redispersibility | Passage through needle bore |
| Composition A | | | X | X | X | X | X |
| Composition A + Nonionic surfactant | Tween 20 | 0.2% | X | Δ | X | X | X |
| | HCO-40 | 0.3% | X | Δ | X | X | X |
| Composition A + p-Hydroxybenzoic acid ester* | M.P. | 0.15% | X | X | X | X | X |
| | B.P. | 0.02% | X | X | X | X | X |
| Composition A + Nonionic surfactant + p-Hydroxybenzoic acid ester* | Tween 20 | 0.2% +M.P. 0.15% | O | O | O | O | O |
| | HCO-60 | 0.2% +B.P. 0.02% | O | O | O | O | O |
| | Pluronic F68 | 0.2% +B.P. 0.015% | O | O | O | O | O |
| | Tween 80 | 0.2% +M.P. 0.15% +B.P. 0.015% | O | O | O | O | O |
| | HCO-50 | 0.3% +E.P. 0.02% +M.P. 0.15% | O | O | O | O | O |

(Note) Dispersion uniformity:
O: The active component particles are evenly dispersed
X: The active component particles are afloat or have settled
Passage through the injection needle bore: With a needle with a bore diameter of 150μ
O: Aspirated easily
Δ: Aspirated with a slight resistance
X: Aspirated with a severe resistance
Redispersibility:
When shaken gently with a hand, it is evenly dispersed.
O: Shaken twice or less
X: Shaken ten or more times
Sedimentation volume:
O: The layer of suspended particles ±30%
X: The layer of suspended particles <30%
*p-Hydroxybenzoic acid ester:
M.P.: Methyl p-hydroxybenzoate
E.P.: Ethyl p-hydroxybenzoate
P.P.: Propyl p-hydroxybenzoate
B.P.: Butyl p-hydroxybenzoate

EXAMPLE 2

Oxendolone acetate: 15 w/v %
Sodium carboxymethylcellulose: 0.7
D-sorbitol: 8
Benzyl alcohol: 1
Tween 20: 0.2
Methyl p-hydroxybenzoate: 0.15
Propyl p-hydroxybenzoate: 0.15

What we claim is:

1. A stabilized aqueous suspension of oxendolone or an ester thereof, which contains 0.05 to 1.0 w/v percent of a nonionic surfactant and 0.01 to 0.25 w/v percent of a p-hydroxybenzoic acid ester.

2. A suspension as claimed in claim 1, wherein the nonionic surfactant is selected from the group consisting of polyoxyethylene sorbitan fatty acid esters, hydrogenated castor oil polyoxyethylene glycol esters and polyoxyethylene polyoxypropylene ethers.

3. A suspension as claimed in claim 1, wherein the HLB number of the nonionic surfactant is within the range of from 8 to 18.

4. A suspension as claimed in claim 1, wherein the p-hydroxybenzoic acid ester is a mixture of methyl p-hydroxybenzoate and propyl p-hydroxybenzoate.

5. A method for preparing a stabilized aqueous suspension of oxendolone or an ester thereof, which comprises by adding 0.05 to 1.0 w/v percent of a nonionic surfactant and 0.01 to 0.25 w/v percent of a p-hydroxybenzoic acid ester.

* * * * *